US010092212B2

(12) United States Patent
Choi

(10) Patent No.: US 10,092,212 B2
(45) Date of Patent: Oct. 9, 2018

(54) POST PROCESSING SYSTEM AND POST PROCESSING METHOD FOR ELECTRICAL IMPEDANCE TOMOGRAPHY IMAGES

(71) Applicant: NATIONAL CHIAO TUNG UNIVERSITY, Hsinchu (TW)

(72) Inventor: Charles Tak-Ming Choi, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 15/649,630

(22) Filed: Jul. 13, 2017

(65) Prior Publication Data
US 2018/0014748 A1    Jan. 18, 2018

(30) Foreign Application Priority Data

Jul. 15, 2016 (TW) .............................. 105122475 A

(51) Int. Cl.
G06K 9/00 (2006.01)
A61B 5/053 (2006.01)
G06N 3/08 (2006.01)
A61B 5/00 (2006.01)

(52) U.S. Cl.
CPC ............ A61B 5/0536 (2013.01); G06N 3/086 (2013.01); A61B 5/7235 (2013.01); G06T 2207/20081 (2013.01)

(58) Field of Classification Search
CPC .... A61B 5/0536; A61B 5/7235; G06N 3/086; G06T 2207/20081
See application file for complete search history.

(56) References Cited

U.S. PATENT DOCUMENTS 6,522,910 B1   2/2003 Gregory
6,725,087 B1   4/2004 Rubinsky et al.
7,490,085 B2   2/2009 Walker et al.
(Continued)

OTHER PUBLICATIONS

Martin, Sébastien, and Charles TM Choi. "Nonlinear electrical impedance tomography reconstruction using artificial neural networks and particle swarm optimization." IEEE Transactions on Magnetics 52.3 (2016): 1-4.*
(Continued)

Primary Examiner — Jonathan S Lee
(74) Attorney, Agent, or Firm — CKC & Partners Co., Ltd.

(57) ABSTRACT

A post processing system for electrical impedance tomography (EIT) images includes a processing device and a post processing device, and the post processing device is coupled to the processing device. The processing device is configured to generate a first EIT image through a solving method based on the measuring data. The measuring data is measured by an electrical impedance tomography instrument. The post processing device is configured to receive the first EIT image and post-process the first EIT image through a neural network algorithm to generate a second EIT image. The neural network algorithm is a feed forward neural network, a recurrent neural network, a convolutional neural network or a deep neural network, and an accuracy of the second electrical impedance tomography image is higher than an accuracy of the first electrical impedance tomography image.

20 Claims, 13 Drawing Sheets

(56) References Cited

U.S. PATENT DOCUMENTS 8,508,238 B2* 8/2013 Mahalingam ........ A61B 5/0536
324/603
2016/0195484 A1* 7/2016 Emery ................... G01R 27/14
702/65

OTHER PUBLICATIONS

T. Meier et al., "Assessment of regional lung recruitment and derecruitment during a PEEP Trial based on electrical impedance tomography", Intensive Care Med, vol. 34, 2008, pp. 543-550.
C. Putensen et al., "Electrical impedance tomography guided ventilation therapy", Current Opinion in Critical Care, vol. 13, 2007, pp. 344-350.
Gordon D. Rubenfeld et al., "Incidence and Outcomes of Acute Lung Injury", The New England Journal of Medicine, Oct. 2005, pp. 1685-1693.
The Acute Respiratory Distress Syndrome Network, "Ventilation with lower tidal volumes as compared with traditional tidal volumes for acute lung injury and the acute respiratory distress syndrome", The New England Journal of Medicine, vol. 342 No. 18, May 2000, pp. 1301-1308.
B. Truyen et al., "Image Reconstruction in Electrical Impedance Tomography: A Selfadaptive Neural Network Approach", Engineering in Medicine and Biology Society, 1993, Proceedings of the 15th Annual International Conference of the IEEE, Oct. 31, 1993, pp. 72-73.

* cited by examiner

100

1400

POST PROCESSING SYSTEM AND POST PROCESSING METHOD FOR ELECTRICAL IMPEDANCE TOMOGRAPHY IMAGES

RELATED APPLICATIONS

This application claims priority to Taiwan Application Serial Number 105122475, filed Jul. 15, 2016, which is herein incorporated by reference.

BACKGROUND

Technical Field

The present invention relates to an image post processing technology. More particularly, the present invention relates to a post processing system and a post processing method for electrical impedance tomography (EIT) images.

Description of Related Art

Electrical impedance tomography (EIT) is a medical imaging technology for generating tomographic images according to conductivity distribution of a certain portion of a body. Compared to other traditional imaging technology, such as positron emission tomography (PET), computed tomography (CT) and magnetic resonance imaging (MRI), electrical impedance tomography is an inexpensive, noninvasive tomographic imaging technology free of ionizing radiation. However, the electrical impedance tomography has a drawback of having poor image resolution, which results from limited number of electrode for data acquisition. Whereas when the number of electrode is increased, cost is also increased and there is a limit of how much resolution can be improved by increasing the number of electrodes, which means that increasing the number of electrode is not a good solution to improve image resolution.

SUMMARY

An aspect of the present disclosure is a post processing system for electrical impedance tomography (EIT) images. The post processing system comprises a processing device and a post processing device, and the post processing device is coupled to the processing device. The processing device is configured to generate a first electrical impedance tomography image through a solving method based on measuring data. The measuring data is measured by an electrical impedance tomography instrument. The post processing device is configured to receive the first electrical impedance tomography image and post-process the first electrical impedance tomography image through a neural network algorithm to generate a second electrical impedance tomography image. The neural network algorithm is a feed forward neural network, a recurrent neural network, a convolutional neural network or a deep neural network, and an accuracy of the second electrical impedance tomography image is higher than an accuracy of the first electrical impedance tomography image.

Another aspect of the present disclosure is a post processing method for electrical impedance tomography images. The post processing method comprises steps as follows. A first electrical impedance tomography image is generated through a solving method based on measuring data by a processing device. The measuring data is measured by an electrical impedance tomography instrument. The first electrical impedance tomography image is post-processed through a neural network algorithm by a post processing device to generate a second electrical impedance tomography image. The neural network algorithm is a feed forward neural network, a recurrent neural network, a convolutional neural network or a deep neural network, and an accuracy of the second electrical impedance tomography image is higher than an accuracy of the first electrical impedance tomography image.

Through the above embodiments, the present disclosure can post-process an electrical impedance tomography image that is generated by using a solving method (e.g., an electrical impedance tomography inverse solving method) through the neural network algorithm to generate an electrical impedance tomography image with higher accuracy. Moreover, the present disclosure can also generate an electrical impedance tomography image with a higher degree of accuracy through the neural network based on the measuring data.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

In order to make the description of the disclosure more detailed and comprehensive, reference will now be made in detail to the accompanying drawings and the following embodiments. However, the provided embodiments are not used to limit the ranges covered by the present disclosure; orders of step description are not used to limit the execution sequence either. Any devices with equivalent effect through rearrangement are also covered by the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise indicated, all numbers expressing quantities, conditions, and the like in the instant disclosure and claims are to be understood as modified in all instances by the term "about." The term "about" refers, for example, to numerical values covering a range of plus or minus 20% of the numerical value. The term "about" preferably refers to numerical values covering range of plus or minus 10% (or most preferably, 5%) of the numerical value. The modifier "about" used in combination with a quantity is inclusive of the stated value.

In this document, the term "coupled" may also be termed as "electrically coupled", and the term "connected" may be termed as "electrically connected," "coupled" and "connected" may also be used to indicate that two or more elements cooperate or interact with each other.

Figure 1:
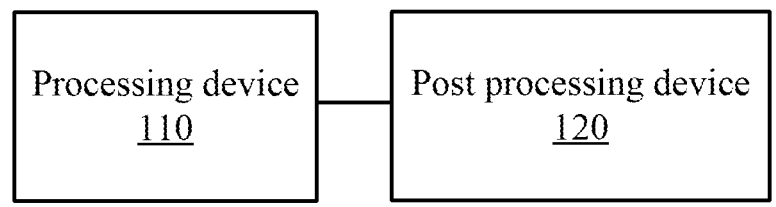
FIG. 1 is a schematic diagram of a post processing system for electrical impedance tomography (EIT) images according to an embodiment of the present disclosure.

Reference is made to FIG. 1. FIG. 1 is a schematic diagram of a post processing system 100 for electrical impedance tomography (EIT) images according to an embodiment of the present disclosure. The post processing system 100 includes a processing device 110 and a post processing device 120. The post processing device 120 is coupled to the processing device 110. The processing device 110 is configured to generate an electrical impedance tomography image based on measuring data. The measuring data is generated by electrical impedance tomography (EIT), electrical resistance tomography (ERT) or electrical capacitance tomography (ECT) instruments.

Specifically, the processing device 110 (e.g., a calculator, a computer, a field-programmable gate array (FPGA), however, the present disclosure is not limited thereto) is configured to generate a first electrical impedance tomography image through a solving method based on the measuring data from EIT instruments. In an embodiment, the solving method is electrical impedance tomography (EIT) inverse solving method. Generally, a first electrical impedance tomography image generated through a solving method (e.g., an electrical impedance tomography inverse solving method) is not identical to the actual image of a target object, that is, there is a problem of distortion. Then, the post processing device 120 (e.g., a FPGA, however, the present disclosure is not limited thereto) is configured to post-process the first electrical impedance tomography image through a neural network (NN) algorithm to generate a second electrical impedance tomography image. In the present embodiment, the neural network algorithm used by the post processing device 120 are trained with images generated from processing device 110 and the actual image of a target object, thus, the neural network algorithm can undistort any images generated from processing device 110. Therefore, compared to the first electrical impedance tomography image, the second electrical impedance tomography image has a higher degree of accuracy. It should be noted that the post processing device 120 uses a trained neural network algorithm to generate the second electrical impedance tomography image. In other words, the post processing device 120 uses the neural network algorithm in an application phase to generate the second electrical impedance tomography image. In another embodiment, electrical impedance tomography instruments and electrical impedance tomography inverse solving methods can be replaced by electrical resistance tomography instruments and electrical resistance tomography inverse solving methods to generate the first electrical resistance tomography image from processing device 110 and second electrical resistance tomography image from post processing device 120. In other embodiment, electrical impedance tomography instruments and electrical impedance tomography inverse solving methods can be replaced by electrical capacitance tomography instruments and electrical capacitance tomography inverse solving method to generate the first electrical capacitance tomography image from processing device 110 and second electrical capacitance tomography image from post processing device 120.

Figure 2A:
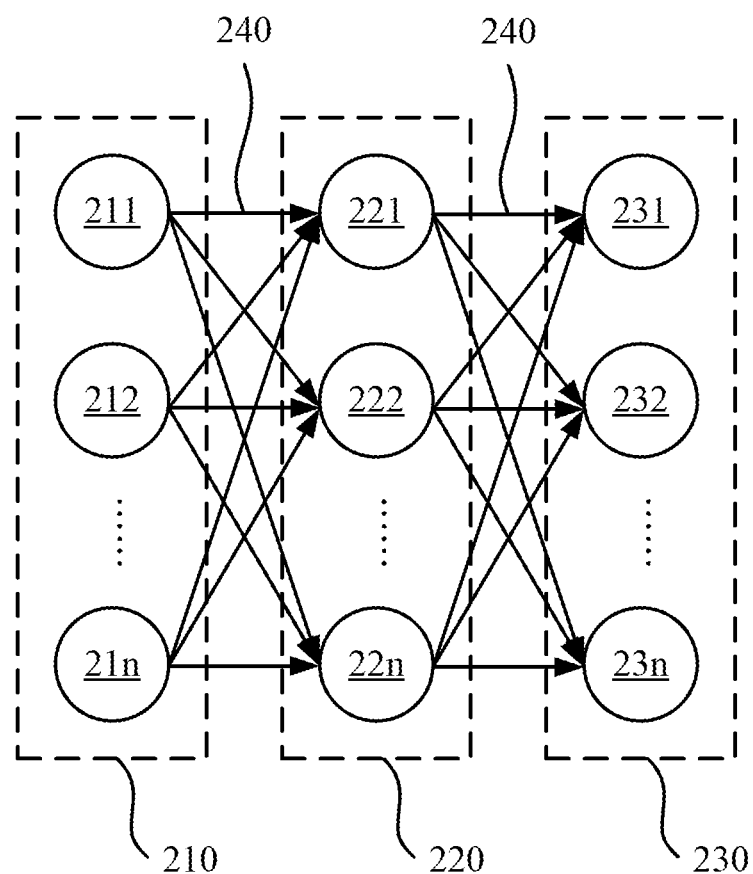
FIGS. 2A-2C are schematic diagrams of neural networks according to some embodiments of the present disclosure.
Figure 2B:
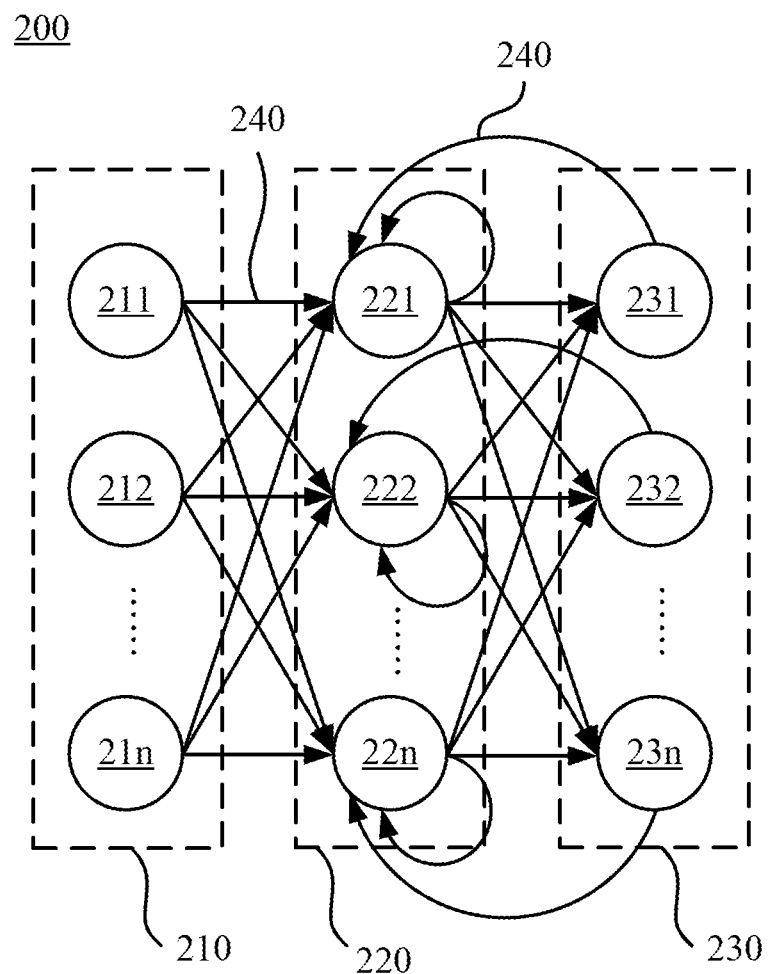
Figure 2C:
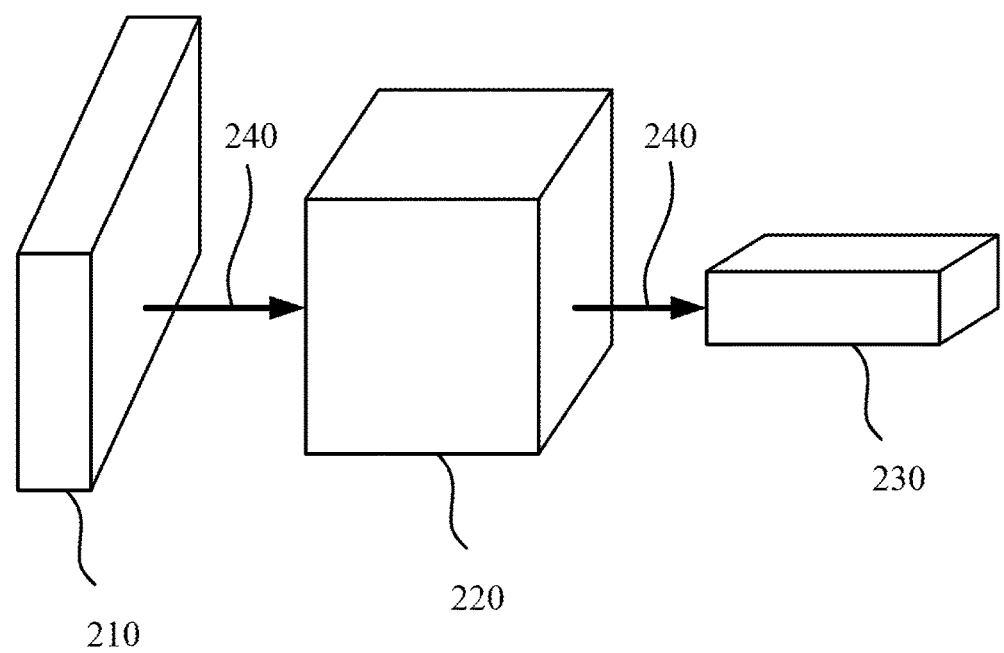

In an embodiment, the neural network algorithm used by the post processing device 120 may be an artificial neural network (ANN) (e.g., feed forward neural network, recurrent neural network or convolutional neural network, however, the present disclosure is not limited thereto) as shown in FIG. 2A-2C. The neural network 200 includes an input layer 210, a hidden layer 220 and an output layer 230. The input layer 210 includes at least one input neuron 211-21$n$, the hidden layer 220 includes at least one hidden neuron 221-22$n$, and the output layer 230 includes at least one output neuron 231-23$n$. There are weighting parameters 240 between the input layer 210 and the hidden layer 220, and between the hidden layer 220 and the output layer 230. In a training phase of the neural network 200, the post processing device 120 may train the neural network 200 through a training image and an actual image to improve accuracy of the second electrical impedance tomography image. Specifically, the post processing device 120 may input at least one training image to the input layer 210, and input at least one actual image to the output layer 230 to determine the weighting parameters 240 between the hidden layer 220 and the input layer 210, and between the at least one hidden layer 220 and the output layer 230. It should be noted that the actual image and the training image have a corresponding relationship. Therefore, the post processing device 120 can input the first electrical impedance tomography image generated under similar measuring condition to the neural network 200 (with the above determined weighting parameters 240) to generate the second electrical impedance tomography image that is a better approximation to the actual image, that is, the second electrical impedance tomography image has a higher degree of accuracy than the first electrical impedance tomography image.

Moreover, in an embodiment, the neural network 200 is a radial basis function (RBF) neural network. The RBF neural network has a hidden layer 220, and the hidden layer 220 is a radial basis function which is represented as follows.

$$y = \sum_j w_j * \exp\left(-\left(\frac{\|x-t\|}{\sigma}\right)^2\right)$$

In the above function, $w_j$ is a weighting parameter of the jth hidden neuron, x is an input vector, t is a center vector of the RBF function (t is usually set as zero), and $\sigma$ is a spread constant. The training process is executed by choosing a center vector t and then fitting the output of the neural network 200 to a linear combination of a RBF function of the input vector x and the weighting parameters $w_j$. If the number of hidden neurons are enough, the RBF neural network can achieve high degree of approximation.

It should be added that the artificial neural network may be a feedforward neural network (as shown in FIG. 2A), a recurrent neural network (as shown in FIG. 2B) or a convolutional neural network (as shown in FIG. 2C). However, the present disclosure is not limited thereto. Moreover, the input layer 210 and the output layer 230 are not limited to a single layer, and can also be plural layers.

Figure 3:
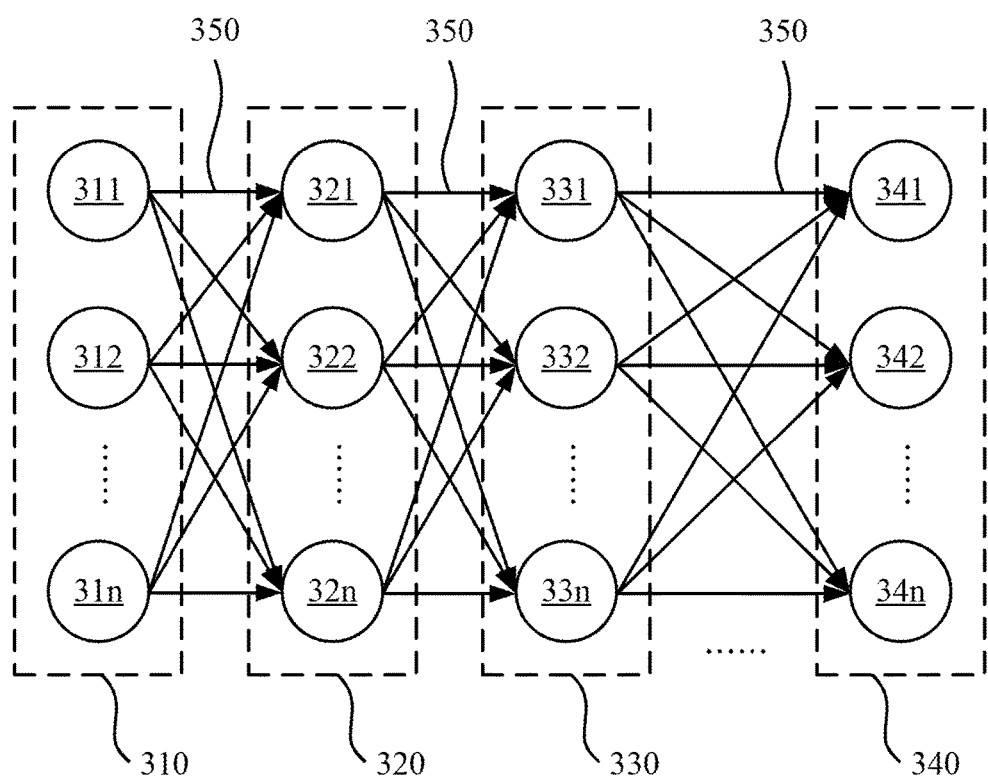
FIG. 3 is a schematic diagram of a neural network according to an embodiment of the present disclosure.

Alternatively, in another embodiment, the neural network algorithm used by the post processing device 120 may be a deep neural network (DNN), as shown in FIG. 3. The neural network 300 includes an input layer 310, a plurality of hidden layers 320, 330 and an output layer 340. The input layer 310 includes at least one input neuron 311-31$n$, the hidden layer 320 includes at least one hidden neuron 321-32$n$, the hidden layer 330 includes at least one hidden neuron 331-33$n$, and the output layer 340 includes at least one output neuron 341-34$n$. There are weighting parameters 350 between the input layer 310 and the hidden layer 320, between the hidden layer 320 and the output layer 340, and between the hidden layer 330 and the output layer 340. As aforementioned, in a training phase of the neural network 300, the post processing device 120 may train the neural network 300 by the training image and the actual image to improve accuracy of the second electrical impedance tomography image, and the description would not be repeated herein. It should be noted that number of the hidden layer in the neural network 300 may be another number, which is not limited to two hidden layers 320, 330, and the weighting parameters 350 between the hidden layers may also be determined through the above training process of the post processing device 120.

Similarly, the deep neural network may be implemented as a feedforward neural network (as shown in FIG. 3), a recurrent neural network or a convolutional neural network. However, the present disclosure is not limited thereto. Moreover, the input layer 310 and the output layer 340 are also not limited to a single layer, and can also be plural layers.

In an embodiment, the solving method may be a linear solving method (e.g., a linear one-step Gauss-Newton algorithm) or a nonlinear solving method (e.g., a primal-dual interior point method (PDIPM) or other iterative methods). In some embodiments, the solving method discussed herein is electrical impedance tomography (EIT) inverse method. For example, the EIT inverse method may be a linear inverse electrical impedance tomography algorithm or a nonlinear iterative inverse electrical impedance tomography method.

In an embodiment, the training images used by the post processing device 120 to train the neural networks 200, 300 may be generated by the processing device 110 through the solving method (e.g., a linear solving method or a nonlinear solving method) based on training data. Similar to the measuring data, the training data is measured by the electrical impedance tomography instrument. Specifically, the user may first use the electrical impedance tomography instrument to measure target objects (with known sizes, shapes and positions) to obtain the training data. Then, the processing device 110 generates the training images through the solving method based on the training data. Generally, the training images generated merely through the solving method is not completely identical to an actual image of the target object, that is, there is a problem of distortion. Therefore, the neural networks 200, 300 trained by the post processing device 120 through the training image and the actual image can effectively generate an electrical impedance tomography image (i.e., the second electrical impedance tomography image) with a higher degree of accuracy than the first electrical impedance tomography image. Moreover, time for generating the second electrical impedance tomography image by the post processing system 100 through the solving method and the neural network algorithm based on the measuring data is very short (e.g., merely about 0.80 seconds, and an actual time for calculation depends on an image size and speeds of the processing device 110 and the post processing device 120).

Alternatively, in another embodiment, the post processing device 120 may post process the first electrical impedance tomography image through the neural network algorithm based on the measuring data to generate a third electrical impedance tomography image. The training method of the neural networks 200, 300 are as aforementioned, and would not be repeated herein. It should be noted that, in the present embodiment, the post processing device 120 may use the measuring data to further calibrate conductance (or impedance) of the electrical impedance tomography image to an actual conductance (or impedance), and therefore the third electrical impedance tomography image has a higher degree of accuracy in conductance distribution than the first electrical impedance tomography image. Moreover, time for generating the third electrical impedance tomography image by the post processing system 100 through the neural network algorithm based on the measuring data is very short (e.g., merely about 0.36 seconds, and an actual time for calculation depends on an image size and speeds of the processing device 110 and the post processing device 120).

As a result, by using the neural network algorithm, the post processing system 100 of the present disclosure can rapidly generate the second electrical impedance tomography image (e.g., a functional electrical impedance tomography image) with a higher degree of accuracy for the image when compare to the first electrical impedance tomography image (which is generated through the solving method). Moreover, the post processing system of the present disclosure can also rapidly generate the third electrical impedance tomography image (e.g., an absolute electrical impedance tomography image) with a higher degree of accuracy for the conductance distribution (when compare with the first electrical impedance tomography image) based on the measuring data and the first electrical impedance tomography image (which is generated through the solving method). In another embodiment, electrical impedance tomography instruments and electrical impedance tomography inverse solving methods can be replaced by electrical resistance tomography instruments and electrical resistance tomography inverse solving methods to generate the first electrical resistance tomography image from the processing device 110 and third electrical resistance tomography image from the post processing device 120 (with ERT measuring data from ERT instruments to calibrate the resistance value for the third ERT images). In other embodiment, electrical impedance tomography instruments and electrical impedance tomography inverse solving methods can be replaced by electrical capacitance tomography instruments and electrical capacitance tomography inverse solving method to generate the first electrical capacitance tomography image from the processing device 110 and third electrical capacitance tomography image from the post processing device 120 (with ECT measuring data from ECT instruments to calibrate the capacitance value for the third ECT images).

It should be added that the second electrical impedance tomography image or the third electrical impedance tomography image generated by the post processing device 120 may be an electrical impedance tomography image formed by relative conductance (or relative impedance) or absolute conductance (or absolute impedance), respectively. In other words, the post processing system of the present disclosure can determine relative conductance or absolute conductance of the electrical impedance tomography image for different demands. In another embodiment, the second ERT images or third ERT images created by the post processing device 120 could be images formed by relative resistance or absolute resistance, respectively. In another embodiment, the second ECT images or third ECT images created by the post processing device 120 could be images formed by relative permittivity or absolute permittivity, respectively.

Since there may be noise in actual measurements, in an embodiment, the post processing device 120 is further configured to determine the weighting parameters 240, 350 based on the training images, which are generated by processing device 110 from training data with known noise values added, and/or known sizes, shapes and positions of the target objects during ANN training. Therefore, the post processing system 100 can further improve accuracy of the electrical impedance tomography image.

In order to describe that the electrical impedance tomography image generated by the post processing system 100 of the present disclosure has a higher degree of accuracy when compared to the prior art, a |ΔRES| error (resolution error) is used to indicate difference between area (or volume in other embodiment) of the target object and area (or volume in other embodiment) of an object in the electrical impedance tomography image. In the prior art, an electrical impedance tomography image generated merely through the linear solving method has a |ΔRES| error of 35.95%, an electrical impedance tomography image generated merely through the nonlinear solving method has a |ΔRES| error of 26.20%. In contrast, an electrical impedance tomography image (i.e., the third electrical impedance tomography image) generated through the neural network algorithm by the post processing system 100 has a |ΔRES| error of 12.54%, and the electrical impedance tomography image (i.e., the second electrical impedance tomography image) generated through the solving method and the neural network algorithm by the post processing system 100 has a |ΔRES| error of 13.29%, in which the neural network is trained with training data without known noise values added (as described above).

As described above, the neural network of the present disclosure trained with the training images, which are generated by processing device 110 from training data with known noise values added, and/or known sizes, shapes and positions of the target objects can improve accuracy. An electrical impedance tomography image (i.e., the third electrical impedance tomography image) generated through the neural network algorithm by the post processing system 100 has a |ΔRES| error (hereinafter referred to as "first error") of 13.02%, and an electrical impedance tomography image (i.e., the second electrical impedance tomography image) generated through the solving method and the neural network algorithm by the post processing system 100 has a |ΔRES| error (hereinafter referred to as "second error") of 13.16%, in which the neural network is trained with training data with known noise values added (as described above). In some preferred conditions, the first error is 11.02%, and the second error is 11.16%.

In order to describe the electrical impedance tomography image generated by the post processing system 100 of the present disclosure, reference is made to FIGS. 4-9.

Figure 4:
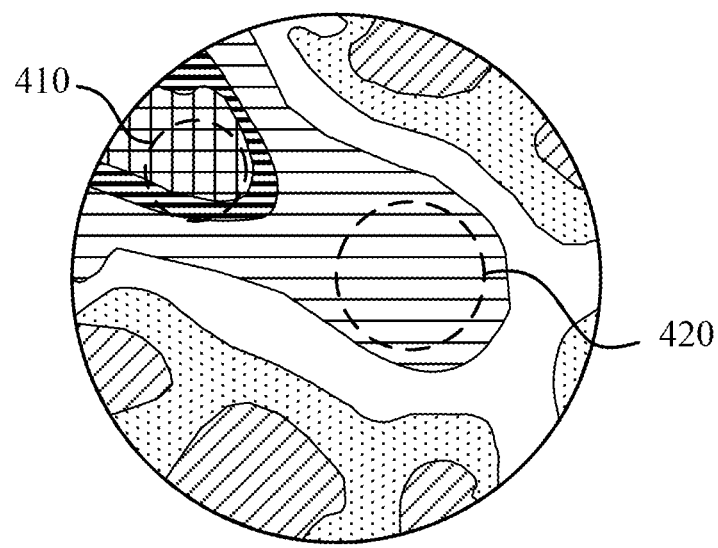
FIGS. 4-9 are schematic diagrams of electrical impedance tomography images according to some embodiments of the present disclosure.

FIG. 4 shows an electrical impedance tomography image generated merely through the linear solving method. As shown in FIG. 4, the electrical impedance tomography image is apparently different from target objects 410, 420, and there are many false images (sometimes also called artifacts) so that the electrical impedance tomography image doesn't have a high accuracy.

Figure 5:
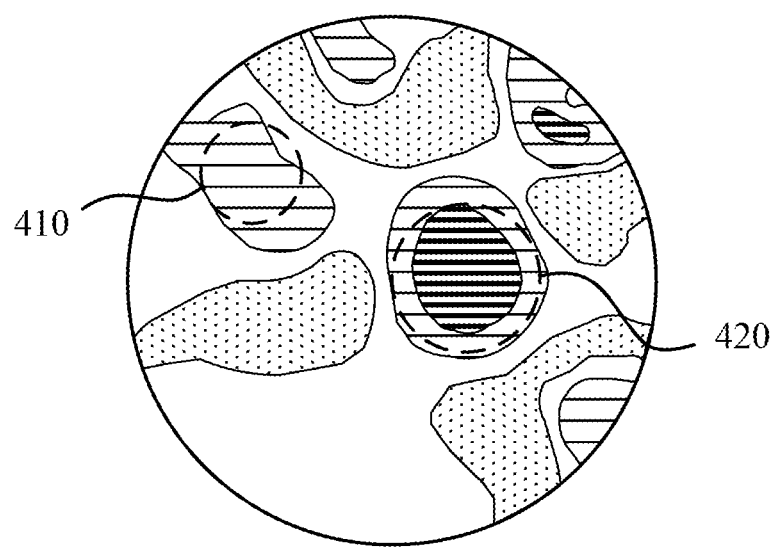

FIG. 5 shows an electrical impedance tomography image generated merely through the nonlinear solving method. As shown in FIG. 5, the electrical impedance tomography image approximately shows the target object 420, but doesn't accurately show the target object 410. Areas outside the target objects 410, 420 also show false images.

Figure 6:
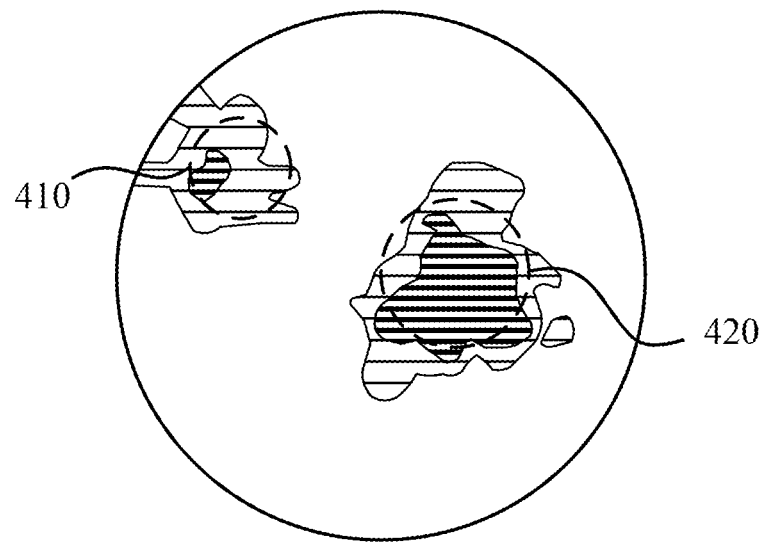

FIG. 6 shows an electrical impedance tomography image (i.e., the third electrical impedance tomography image) generated merely through the neural network algorithm. The neural networks 200, 300 are trained by training data (without known noise values added) only (as described above). As shown in FIG. 6, the electrical impedance tomography image approximately shows the target object 420 and the target object 410, and areas outside the target objects 410, 420 don't show any false images.

Figure 7:
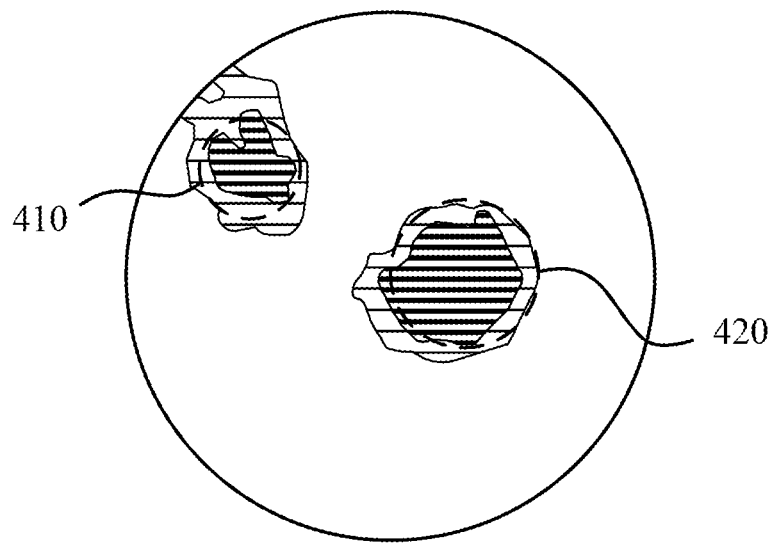

FIG. 7 shows an electrical impedance tomography image (i.e., the second electrical impedance tomography image) generated through the solving method and the neural network algorithm. The neural networks 200, 300 are trained with training data (without known noise values added) only (as described above). As shown in FIG. 7, the electrical impedance tomography image approximately shows the target object 420 and the target object 410, and areas outside the target objects 410, 420 don't show any false images.

Figure 8:
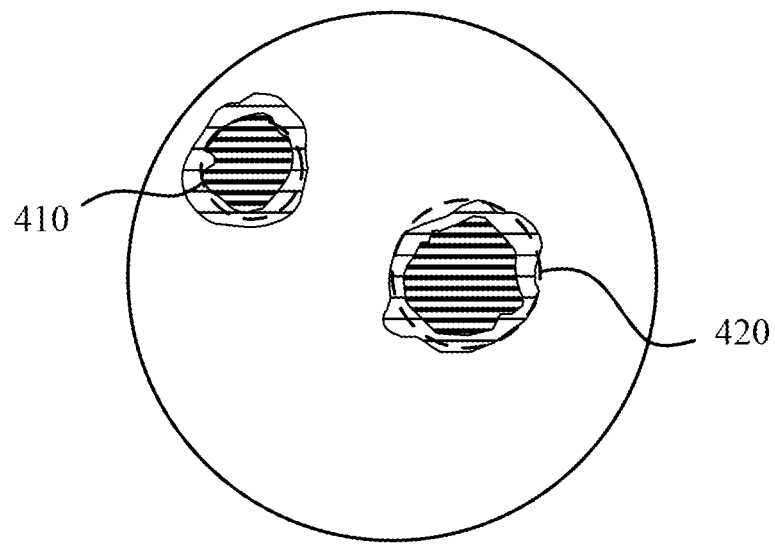

FIG. 8 shows an electrical impedance tomography image (i.e., the third electrical impedance tomography image) generated through the neural network algorithm. The neural networks 200, 300 are trained by training data with known noise values added (as described above). As shown in FIG. 8, the electrical impedance tomography image approximately shows the target object 420 and the target object 410, and areas outside the target objects 410, 420 don't show any false images.

Figure 9:
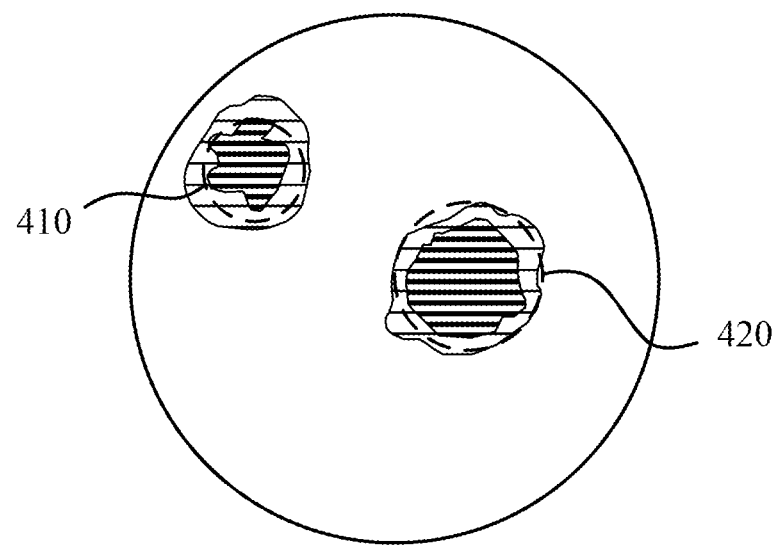

FIG. 9 shows an electrical impedance tomography image (i.e., the second electrical impedance tomography image) generated through the solving method and the neural network algorithm. The neural networks 200, 300 are trained by training data with known noise values added (as described above). As shown in FIG. 9, the electrical impedance tomography image approximately shows the target object 420 and the target object 410, and areas outside the target objects 410, 420 don't show any false images.

Therefore, compared to the electrical impedance tomography images (as shown in FIGS. 4-5) generated merely through the solving method, the electrical impedance tomography images (as shown in FIGS. 6-9) generated through the neural network algorithm have a higher degree of accuracy. Moreover, the post processing system 100 of the present disclosure can also integrate the neural network algorithm and the solving method or use training data with known noise values added (as described above) for training the neural network to further improve accuracy.

Figure 10:
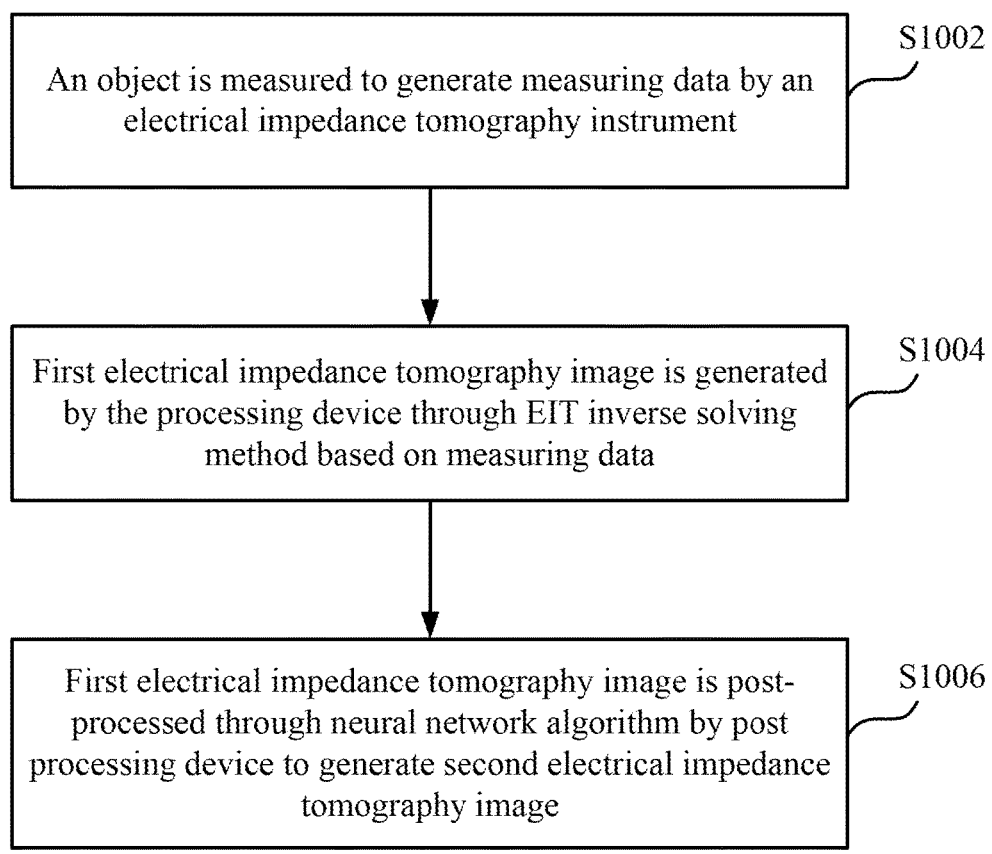
FIG. 10 is a flow chart of a post processing method for electrical impedance tomography images according to an embodiment of the present disclosure.

FIG. 10 is a flow chart of a post processing method 1000 for electrical impedance tomography images according to an embodiment of the present disclosure. The post processing method 1000 includes steps S1002-S1006, and the post processing method 1000 can be applied to the post processing system 100 as shown in FIG. 1. However, those skilled in the art should understand that the mentioned steps in the present embodiment are in an adjustable execution sequence according to the actual demands except for the steps in a specially described sequence, and even the steps or parts of the steps can be executed simultaneously.

In step S1002, an object is measured to generate measuring data by an electrical impedance tomography instrument.

In step S1004, a first electrical impedance tomography image is generated through an electrical impedance tomography (EIT) inverse solving method based on the measuring data by a processing device.

In step S1006, the first electrical impedance tomography image is post-processed through a neural network algorithm by a post processing device to generate a second electrical impedance tomography image.

Figure 11:
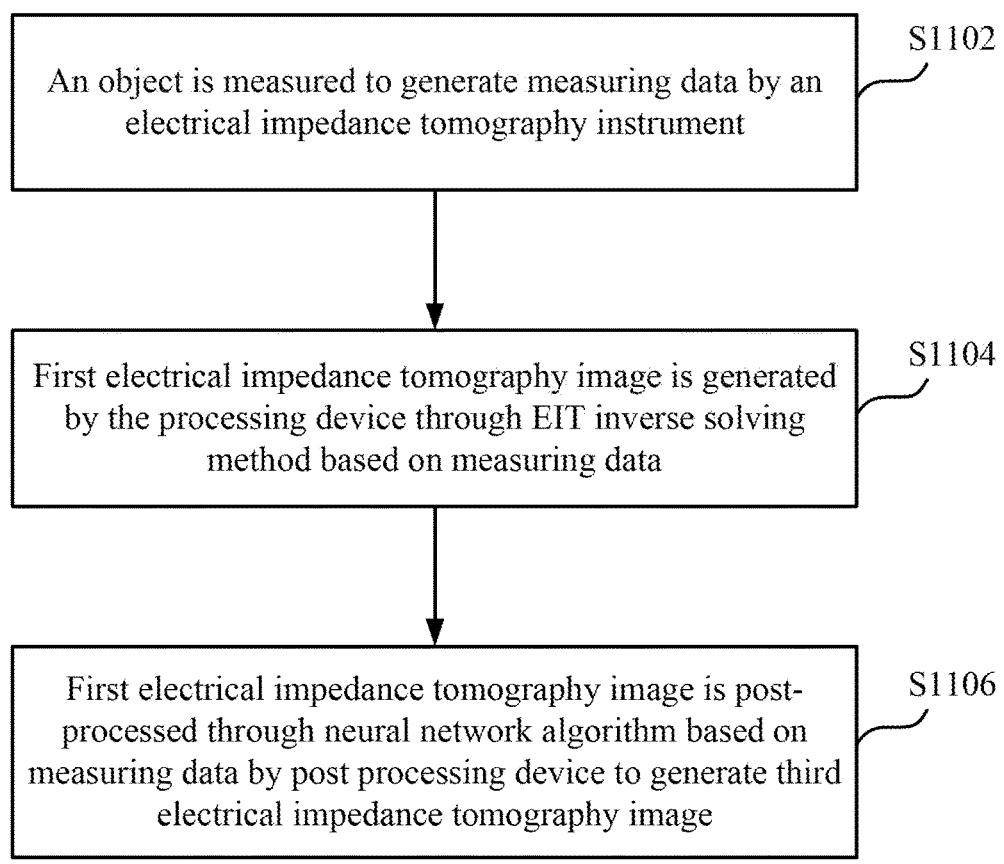
FIG. 11 is a flow chart of a post processing method for electrical impedance tomography images according to an embodiment of the present disclosure.

FIG. 11 is a flow chart of a post processing method 1100 for electrical impedance tomography images according to an embodiment of the present disclosure. The post processing method 1100 includes steps S1102-S1106, and the post processing method 1100 can be applied to the post processing system 100 as shown in FIG. 1. However, those skilled in the art should understand that the mentioned steps in the present embodiment are in an adjustable execution sequence according to the actual demands except for the steps in a specially described sequence, and even the steps or parts of the steps can be executed simultaneously.

In step S1102, an object is measured to generate measuring data by an electrical impedance tomography instrument.

In step S1104, a first electrical impedance tomography image is generated through the electrical impedance tomography (EIT) inverse solving method based on the measuring data by a processing device.

In step S1106, the first electrical impedance tomography image is post-processed through a neural network algorithm based on the measuring data by a post processing device to generate a third electrical impedance tomography image.

Figure 12:
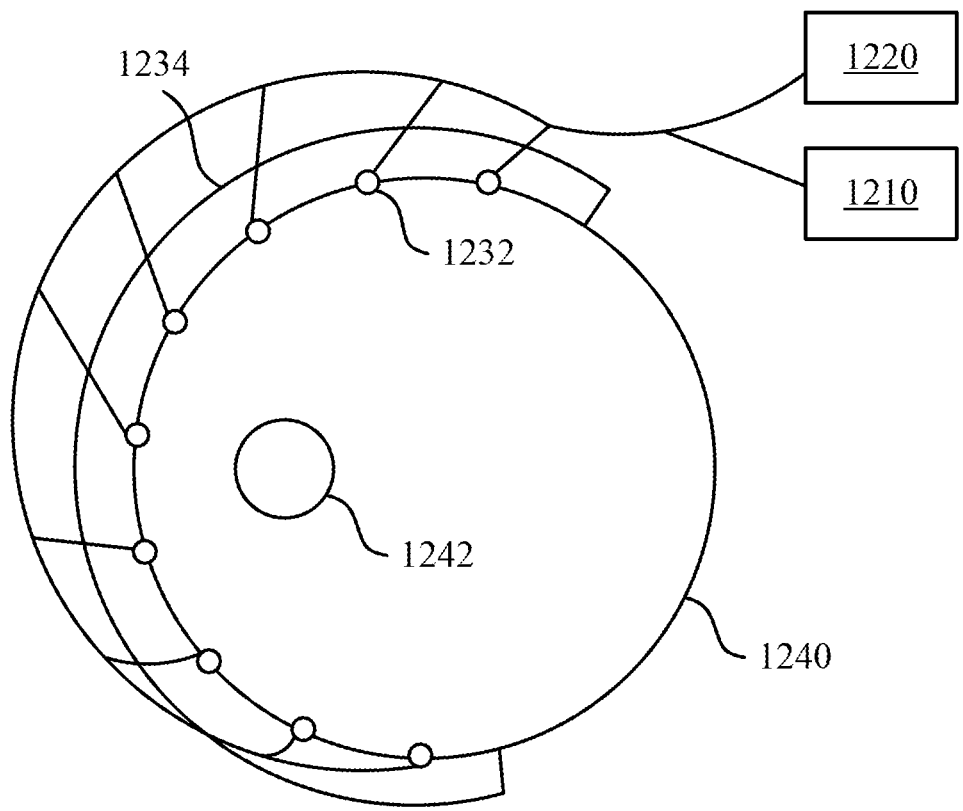
FIG. 12 is a schematic diagram of an electrical impedance tomography instrument according to an embodiment of the present disclosure.
Figure 13:
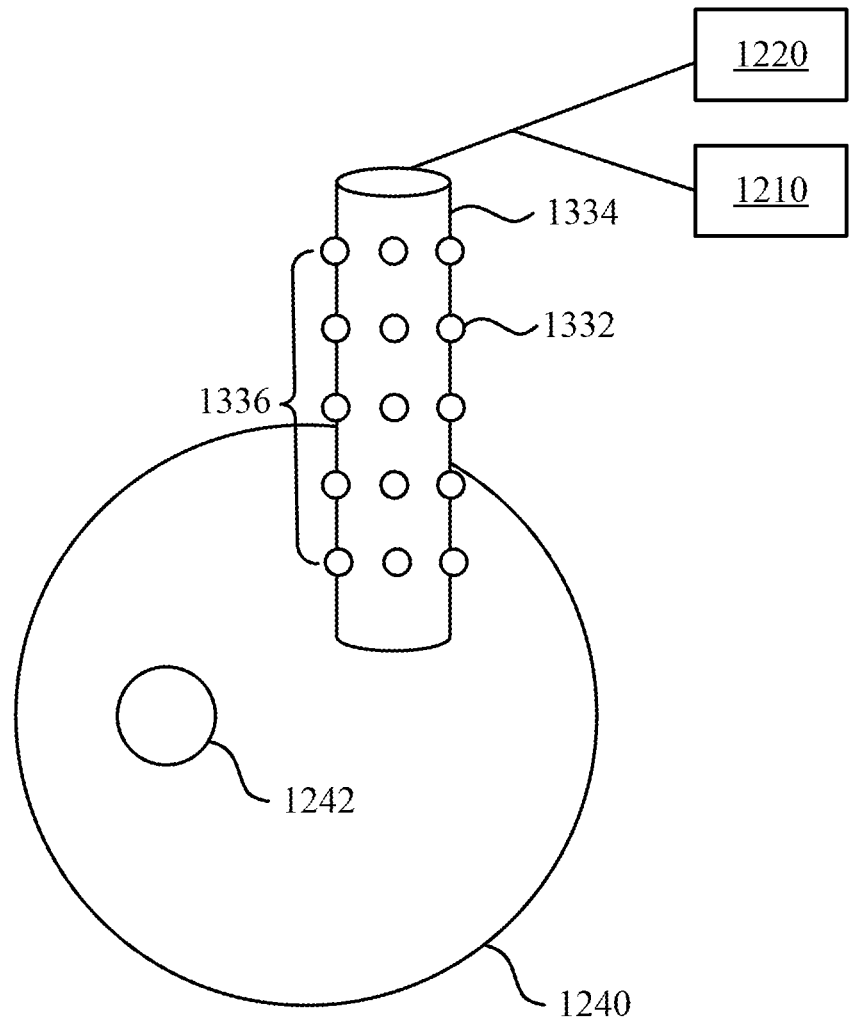
FIG. 13 is a schematic diagram of an electrical impedance tomography instrument according to an embodiment of the present disclosure.

In order to illustrate examples of electrical impedance tomography instruments, reference is made to FIGS. 12, 13. FIG. 12 shows an example of an inward-looking electrical impedance tomography instrument. As shown in FIG. 12, the electrical impedance tomography instrument includes a plurality of electrodes 1232, a bearing surface 1234, an electrode controller 1210 and a data acquisition device 1220. The bearing surface 1234 is a 3D (or 2D) curved surface, and covers an object 1240 to be measured. Therefore, the electrodes 1232 are attached on a surface of the object 1240.

The electrode controller 1210 is electrical connected to the electrodes 1232 to drive the electrodes 1232 sequentially or simultaneously. The data acquisition device 1220 is configured to collect and analyze signals detected from the electrodes 1232. There is a different area 1242 within the object 1240, and the different area 1242 is the target of detection and analysis by the electrical impedance tomography instrument.

In order to describe different measuring methods, reference is made to FIG. 13. FIG. 13 shows an example of an outward-looking electrical impedance tomography instrument. As shown in FIG. 13, the electrical impedance tomography instrument includes a plurality of electrodes 1332, a bearing surface 1334, an electrode controller 1210 and a data acquisition device 1220. The bearing surface 1334 is cylinder-shaped (in other embodiments, it could be spherical-shaped or other arbitrary shapes) and an electrode array 1336 composed of the electrodes 1332 is attached on the bearing surface. The same configuration as the configuration in FIG. 12 would not be repeated herein.

Through the above embodiments, the present disclosure can post-process the electrical impedance tomography image that is generated by the solving method through the neural network algorithm to generate the electrical impedance tomography image with a higher degree of accuracy. Moreover, the present disclosure can also generate the electrical impedance tomography image with a higher degree of accuracy through the neural network based on the measuring data.

Differences between embodiments of the present disclosure and related approaches will be discussed in the following paragraphs. First of all, according to the technology disclosed in U.S. Pat. No. 6,522,910B1, neural network analysis and scale factors are used to generate enhanced information of the electrical properties of the sample. In other words, image size is adjusted according to the scale factors through the neural network, and accuracy of image is not improved in U.S. Pat. No. 6,522,910B1. In comparison, in the present disclosure, the post processing system 100 improves an accuracy of the second electrical impedance tomography image.

According to the technology disclosed in U.S. Pat. No. 7,490,085B2, EIT (and other imaging methods) is used and then computer assisted data algorithm (including artificial neural network) is used for identifying features of interest (e.g., breast cancer, etc). In comparison, in the present disclosure, a feed forward neural network, a recurrent neural network, a convolutional neural network or a deep neural network is used to generate an EIT image with a higher degree of accuracy (i.e., reducing error of the EIT image) rather than identifying specific features of the EIT image.

Figure 14:
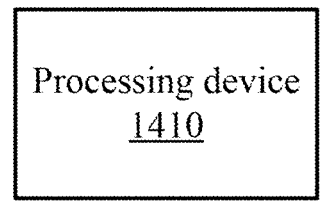
FIG. 14 is a schematic diagram of a processing system according to some related approaches.

According to the technology disclosed in B. Truyen, J. Cornelis, P. Vandervelden, "Image reconstruction in electrical impedance tomography: a self adaptive neural network approach," Engineering in Medicine and Biology Society, 1993. Proceedings of the 15th Annual International Conference of the IEEE, 31 Oct. 1993, page 72-73, a processing device 1410 of a processing system 1400 (as shown in FIG. 14) uses a recurrent neural network to replace EIT, and thus it does not require matrix inversion or matrix factorization as required in EIT inverse solving method, that is, the processing device 1410 does not use the recurrent neural network for post-processing. In comparison, in the present disclosure, the processing device 110 generate the first electrical impedance tomography image through the solving method (e.g., matrix inversion or matrix factorization) based on measuring data from an electrical impedance tomography instrument, and the post processing device 120 post-processes the first electrical impedance tomography image through the neural network algorithm to generate a second electrical impedance tomography image with a higher degree of accuracy.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A post processing system for electrical impedance tomography (EIT) images, comprising:
a processing device configured to generate a first electrical impedance tomography image through a first solving method based on measuring data, wherein the measuring data is measured by an electrical impedance tomography instrument; and a post processing device coupled to the processing device and configured to receive the first electrical impedance tomography image and post-process the first electrical impedance tomography image through a neural network algorithm to generate a second electrical impedance tomography image, wherein the neural network algorithm is a feed forward neural network, a recurrent neural network, a convolutional neural network or a deep neural network, and an accuracy of the second electrical impedance tomography image is higher than an accuracy of the first electrical impedance tomography image.

2. The post processing system of claim 1, wherein the post processing device is further configured to post-process the first electrical impedance tomography image through the neural network algorithm based on the measuring data to generate a third electrical impedance tomography image.

3. The post processing system of claim 1, wherein the neural network algorithm comprises at least one input layer, at least one output layer and at least one hidden layer, and the post processing device is further configured to input at least one training image to the at least one input layer and input at least one actual image corresponding to the at least one training image to the at least one output layer to determine a plurality of weighting parameters between the at least one hidden layer and the at least one input layer, and between the at least one hidden layer and the at least one output layer.

4. The post processing system of claim 3, wherein the processing device is further configured to generate the at least one training image through the first solving method based on at least one training data and send the at least one training image to the post processing device, wherein the at least one training data is measured by the electrical impedance tomography instrument.

5. The post processing system of claim 3, wherein the post processing device is further configured to determine the weighting parameters based on the at least one training image generated by the processing device from at least one training data, with noise added.

6. The post processing system of claim 5, wherein the post processing device is further configured to determine the weighting parameters based on the at least one training image generated by the processing device, with sizes, shapes and positions of target objects.

7. The post processing system of claim 1, wherein the first solving method is a linear inverse electrical impedance tomography algorithm.

8. The post processing system of claim 1, wherein the first solving method is a nonlinear iterative inverse electrical impedance tomography method.

9. The post processing system of claim 1, wherein the processing device is further configured to generate a first electrical resistance tomography image through a second solving method based on measuring data, wherein the measuring data is measured by an electrical resistance tomography instrument; and the post processing device is further configured to receive the first electrical resistance tomography image and post-process the first electrical resistance tomography image through the neural network algorithm to generate a second electrical resistance tomography image, wherein the neural network algorithm is the feed forward neural network, the recurrent neural network, the convolutional neural network or the deep neural network, and an accuracy of the second electrical resistance tomography image is higher than an accuracy of the first electrical resistance tomography image.

10. The post processing system of claim 1, wherein the processing device is further configured to generate a first electrical capacitance tomography image through a third solving method based on measuring data, wherein the measuring data is measured by an electrical capacitance tomography instrument; and the post processing device is further configured to receive the first electrical capacitance tomography image and post-process the first electrical capacitance tomography image through the neural network algorithm to generate a second electrical capacitance tomography image, wherein the neural network algorithm is the feed forward neural network, the recurrent neural network, the convolutional neural network or the deep neural network, and an accuracy of the second electrical capacitance tomography image is higher than an accuracy of the first electrical capacitance tomography image.

11. A post processing method for electrical impedance tomography images, comprising:

by a processing device, generating a first electrical impedance tomography image through a first solving method based on measuring data, wherein the measuring data is measured by an electrical impedance tomography instrument; and by a post processing device, post-processing the first electrical impedance tomography image through a neural network algorithm to generate a second electrical impedance tomography image, wherein the neural network algorithm is a feed forward neural network, a recurrent neural network, a convolutional neural network, or a deep neural network, and an accuracy of the second electrical impedance tomography image is higher than an accuracy of the first electrical impedance tomography image.

12. The post processing method of claim 11, further comprising:

by the post processing device, post-processing the first electrical impedance tomography image through the neural network algorithm based on the measuring data to generate a third electrical impedance tomography image.

13. The post processing method of claim 11, wherein the neural network algorithm comprises at least one input layer, at least one output layer and at least one hidden layer, and the post processing method further comprises:

by the post processing device, inputting at least one training image to the at least one input layer, and inputting at least one actual image corresponding to the at least one training image to the at least one output layer to determine a plurality of weighting parameters between the at least one hidden layer and the at least one input layer, and between the at least one hidden layer and the at least one output layer.

14. The post processing method of claim 13, further comprising:

by the processing device, generating the at least one training image through the first solving method based on at least one training data, wherein the at least one training data is measured by the electrical impedance tomography instrument.

15. The post processing method of claim 13, further comprising:

by the post processing device, determining the weighting parameters based on the at least one training image generated by the processing device from at least one training data, with noise added.

16. The post processing method of claim 15, further comprising:
by the post processing device, determining the weighting parameters based on the at least one training image generated by the processing device, with sizes, shapes and positions of target objects.

17. The post processing method of claim 11, wherein the first solving method is a linear inverse electrical impedance tomography algorithm.

18. The post processing method of claim 11, wherein the first solving method is a nonlinear iterative inverse electrical impedance tomography method.

19. The post processing method of claim 11, further comprising:
by the processing device, generating a first electrical resistance tomography image through a second solving method based on measuring data, wherein the measuring data is measured by an electrical resistance tomography instrument; and
by the post processing device, post-processing the first electrical resistance tomography image through the neural network algorithm to generate a second electrical resistance tomography image, wherein the neural network algorithm is the feed forward neural network, the recurrent neural network, the convolutional neural network, or the deep neural network, and an accuracy of the second electrical resistance tomography image is higher than an accuracy of the first electrical resistance tomography image.

20. The post processing method of claim 11, further comprising:
by the processing device, generating a first electrical capacitance tomography image through a third solving method based on measuring data, wherein the measuring data is measured by an electrical capacitance tomography instrument; and
by the post processing device, post-processing the first electrical capacitance tomography image through the neural network algorithm to generate a second electrical capacitance tomography image, wherein the neural network algorithm is a feed forward neural network, a recurrent neural network, a convolutional neural network, or a deep neural network, and an accuracy of the second electrical capacitance tomography image is higher than an accuracy of the first electrical capacitance tomography image.

* * * * *

UNITED STATES PATENT AND TRADEMARK OFFICE
CERTIFICATE OF CORRECTION

PATENT NO. : 10,092,212 B2
APPLICATION NO. : 15/649630
DATED : October 9, 2018
INVENTOR(S) : Choi et al.

Page 1 of 1

It is certified that error appears in the above-identified patent and that said Letters Patent is hereby corrected as shown below:

On the Title Page

Item (12) "Choi" should read -- Choi, et al. --.

Item (72) Inventor is corrected to read:
-- Charles Tak-Ming Choi, Hsinchu (TW);
Sébastien Martin, Cormontreuil (FR) --.

Signed and Sealed this
Fourteenth Day of May, 2019

Andrei Iancu
*Director of the United States Patent and Trademark Office*